US008349302B2

(12) United States Patent
Johnson et al.

(10) Patent No.: US 8,349,302 B2
(45) Date of Patent: **\*Jan. 8, 2013**

(54) SHAMPOO CONTAINING A GEL NETWORK AND A NON-GUAR GALACTOMANNAN POLYMER DERIVATIVE

(75) Inventors: Eric Scott Johnson, Hamilton, OH (US); Jennifer Elaine Hilvert, Cincinnati, OH (US); Benjamin Parker Heath, Cincinnati, OH (US); Sarah Elizabeth Cooper, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1307 days.

This patent is subject to a terminal disclaimer.

(21) Appl. No.: 11/475,485

(22) Filed: Jun. 27, 2006

(65) Prior Publication Data

US 2006/0269502 A1 Nov. 30, 2006

Related U.S. Application Data

(63) Continuation-in-part of application No. 11/228,770, filed on Sep. 16, 2005, which is a continuation-in-part of application No. 10/454,433, filed on Jun. 4, 2003, now Pat. No. 7,303,744.

(60) Provisional application No. 60/385,641, filed on Jun. 4, 2002.

(51) Int. Cl.
*A61Q 5/02* (2006.01)

(52) U.S. Cl. .............. 424/70.19; 424/70.21; 424/70.22; 424/70.28; 424/70.31

(58) Field of Classification Search ........................ None
See application file for complete search history.

(56) References Cited

U.S. PATENT DOCUMENTS

| | | |
|---|---|---|
| 2,396,278 A | 3/1946 | Lind et al. |
| 2,438,091 A | 3/1948 | Lynch et al. |
| 2,486,921 A | 11/1949 | Byerly et al. |
| 2,486,922 A | 11/1949 | Strain et al. |
| 2,528,378 A | 10/1950 | Manheimer et al. |
| 2,658,072 A | 11/1953 | Kosmin et al. |
| 2,694,668 A | 11/1954 | Pricke et al. |
| 2,786,847 A | 3/1957 | Cislak et al. |
| 2,798,053 A | 7/1957 | Brown et al. |
| 2,809,971 A | 10/1957 | Berstein et al. |
| 2,826,551 A | 3/1958 | Geen et al. |
| 3,152,046 A | 10/1964 | Kapral et al. |
| 3,155,591 A | 11/1964 | Hilfer et al. |
| 2,326,733 A | 2/1966 | Karsten et al. |
| 3,236,733 A | 2/1966 | Karsten et al. |
| 3,332,880 A | 7/1967 | Kessler et al. |
| 3,589,999 A | 6/1971 | McRae et al. |
| 3,590,035 A | 6/1971 | Damico et al. |
| 3,753,196 A | 8/1973 | Kurtz et al. |
| 3,761,418 A | 9/1973 | Parran et al. |
| 3,773,770 A | 11/1973 | Damico et al. |
| 3,852,441 A | 12/1974 | Kooistra et al. |
| 3,929,678 A | 12/1975 | Laughlin et al. |
| 3,940,482 A | 2/1976 | Grand et al. |
| 3,958,581 A | 5/1976 | Abegg et al. |
| 3,959,461 A | 5/1976 | Bailey et al. |
| 3,964,500 A | 6/1976 | Drakoff et al. |
| 4,055,655 A | 10/1977 | Maurer et al. |
| 4,089,945 A | 5/1978 | Brinkman et al. |
| 4,152,416 A | 5/1979 | Spitzer et al. |
| 4,161,526 A | 7/1979 | Gorman et al. |
| 4,197,865 A | 4/1980 | Jacquet et al. |
| 4,217,914 A | 8/1980 | Jacquet et al. |
| 4,323,683 A | 4/1982 | Bolich et al. |
| 4,345,080 A | 8/1982 | Bolich et al. |
| 4,364,387 A | 12/1982 | Larkin et al. |
| 4,379,753 A | 4/1983 | Bolich et al. |
| 4,381,919 A | 5/1983 | Jacquet et al. |
| 4,387,090 A | 6/1983 | Bolich et al. |
| 4,422,853 A | 12/1983 | Jacquet et al. |
| 4,470,982 A | 9/1984 | Winkler et al. |
| 4,507,280 A | 3/1985 | Pohl et al. |
| 4,529,586 A | 7/1985 | DeMarco et al. |
| 4,565,647 A | 1/1986 | Llenado et al. |
| 4,608,183 A | 8/1986 | Rossmoore et al. |
| 4,663,158 A | 5/1987 | Wolfram et al. |
| 4,666,616 A | 5/1987 | Rossmoore et al. |
| 4,670,430 A | 6/1987 | Imamura et al. |

(Continued)

FOREIGN PATENT DOCUMENTS

CN 1658830 A 8/2005

(Continued)

OTHER PUBLICATIONS

U.S. Appl. No. 11/475,484, filed Jun. 27, 2006, Johnson.
Eccleston, et al., "Functions of mixed Emulsifiers and Emulsifying Waxes in Dermatological Lotions and Creams", *Colloids and Surfaces*, May 15, 1997, pp. 169-182, vol. 123-124, A. Physicachemicl and Engineering Aspects, Elsevier, Amsterdam, NL, XP000509628.
Ribeiro, H.M., et al, "Structure and rheology of semisolid o/w creams containing cetyl alcohol/non-ionic surfactant mixed emulsifier and different polymers", *International Journal of Cosmetic Science*, 2004, pp. 47-59, vol. 26, No. 2, Blackwell Publishing Ltd, XP002413735.

(Continued)

*Primary Examiner* — Jyothsna Venkat
(74) *Attorney, Agent, or Firm* — Angela K. Haughey

(57) ABSTRACT

Shampoo compositions comprise (a) from about 5% to about 50% of one or more detersive surfactants; (b) a dispersed gel network phase comprising: (i) at least about 0.05% of one or more fatty amphiphiles; (ii) at least about 0.01% of one or more secondary surfactants; and (iii) water; (c) at least about 0.05% of a galactomannan polymer derivative with a net positive charge and having a mannose to galactose ratio of greater than 2:1 on a monomer to monomer basis, wherein the galactomannan polymer derivative has: (i) a molecular weight from about 1,000 to about 10,000,000; and (ii) a cationic charge density from about 0.7 meq/g to about 7 meq/g; and (d) at least about 20% of an aqueous carrier; all by weight of the shampoo composition.

9 Claims, No Drawings

U.S. PATENT DOCUMENTS

| | | | |
|---|---|---|---|
| 4,686,254 | A | 8/1987 | Lochhead et al. |
| 4,704,272 | A | 11/1987 | Oh et al. |
| 4,708,863 | A | 11/1987 | Bews et al. |
| 4,788,006 | A | 11/1988 | Bolich et al. |
| 4,834,767 | A | 5/1989 | Helioff et al. |
| 4,885,107 | A | 12/1989 | Wetzel et al. |
| 4,898,585 | A | 2/1990 | Borsanyi et al. |
| 5,034,218 | A | 7/1991 | Duvel et al. |
| 5,057,153 | A | 10/1991 | Ruggiero et al. |
| 5,104,646 | A | 4/1992 | Bolich et al. |
| 5,106,609 | A | 4/1992 | Bolich et al. |
| 5,106,613 | A | 4/1992 | Hartnett et al. |
| 5,114,898 | A | 5/1992 | Pinnavaia et al. |
| 5,154,847 | A | 10/1992 | LaPetina et al. |
| 5,186,928 | A | 2/1993 | Birtwistle et al. |
| 5,202,048 | A | 4/1993 | Bartolo et al. |
| 5,227,156 | A | 7/1993 | Wiese et al. |
| 5,248,445 | A | 9/1993 | Rizvi et al. |
| RE34,584 | E | 4/1994 | Grote et al. |
| 5,358,667 | A | 10/1994 | Bergmann et al. |
| 5,462,589 | A | 10/1995 | Nicholas et al. |
| 5,466,425 | A | 11/1995 | Adams et al. |
| 5,478,501 | A | 12/1995 | Rau |
| 5,518,774 | A | 5/1996 | Kappock et al. |
| 5,540,954 | A | 7/1996 | Nicholas et al. |
| 5,562,995 | A | 10/1996 | Kappock et al. |
| 5,614,538 | A | 3/1997 | Nelson et al. |
| 5,674,478 | A | 10/1997 | Dodd et al. |
| 5,696,169 | A | 12/1997 | Arima et al. |
| 5,710,114 | A | 1/1998 | Pyles et al. |
| 5,726,137 | A | 3/1998 | Patel et al. |
| 5,750,122 | A | 5/1998 | Evans et al. |
| 5,756,076 | A | 5/1998 | Cervantes et al. |
| 5,785,962 | A * | 7/1998 | Hinz et al. ................ 424/70.22 |
| 5,798,121 | A | 8/1998 | Cauwet et al. |
| 5,837,661 | A | 11/1998 | Evans et al. |
| 5,853,707 | A | 12/1998 | Wells |
| 5,854,319 | A | 12/1998 | O'Lenick et al. |
| 5,874,476 | A | 2/1999 | Hsu et al. |
| 5,876,705 | A | 3/1999 | Uchiyama et al. |
| 5,880,076 | A | 3/1999 | Vermeer et al. |
| 5,883,154 | A | 3/1999 | Kappock et al. |
| 5,939,059 | A | 8/1999 | Franklin et al. |
| 5,939,203 | A | 8/1999 | Kappock et al. |
| 5,955,066 | A | 9/1999 | Sako et al. |
| 5,965,515 | A | 10/1999 | Rau |
| 5,997,851 | A | 12/1999 | Cox et al. |
| 6,017,562 | A | 1/2000 | Kaufman et al. |
| 6,034,043 | A | 3/2000 | Fujiwara et al. |
| 6,303,109 | B1 | 10/2001 | Foerster et al. |
| 6,309,628 | B1 | 10/2001 | Ansmann et al. |
| 6,333,040 | B1 | 12/2001 | Boyxen et al. |
| RE37,793 | E | 7/2002 | Domenico et al. |
| 6,495,538 | B2 | 12/2002 | Fliss et al. |
| 6,521,238 | B1 | 2/2003 | Muller et al. |
| RE38,130 | E | 6/2003 | Adams |
| 6,719,967 | B1 | 4/2004 | Brown |
| 6,774,096 | B1 | 8/2004 | Paye et al. |
| 6,908,912 | B2 | 6/2005 | Rioux et al. |
| 7,303,744 | B2 * | 12/2007 | Wells et al. ................ 424/70.28 |
| 2001/0047039 | A1 | 11/2001 | McManus et al. |
| 2002/0012646 | A1 | 1/2002 | Royce et al. |
| 2002/0119113 | A1 | 8/2002 | Ellis et al. |
| 2002/0169283 | A1 | 11/2002 | Lu et al. |
| 2003/0095938 | A1 | 5/2003 | Casero et al. |
| 2003/0119805 | A1 | 6/2003 | Fliss et al. |
| 2003/0130145 | A1 | 7/2003 | Patel et al. |
| 2003/0171231 | A1 | 9/2003 | Shana'a et al. |
| 2003/0185779 | A1 | 10/2003 | Mitsumatsu et al. |
| 2003/0215522 | A1 | 11/2003 | Johnson et al. |
| 2003/0223952 | A1 | 12/2003 | Wells et al. |
| 2003/0224955 | A1 | 12/2003 | Ribery et al. |
| 2004/0058855 | A1 | 3/2004 | Schwartz et al. |
| 2004/0167114 | A1 | 8/2004 | Fliss et al. |
| 2004/0191331 | A1 | 9/2004 | Schwartz et al. |
| 2004/0197294 | A1 | 10/2004 | Seipel et al. |
| 2004/0223941 | A1 | 11/2004 | Schwartz et al. |
| 2004/0234471 | A1 | 11/2004 | Corbella |
| 2004/0266886 | A1 | 12/2004 | Seipel et al. |
| 2005/0031569 | A1 | 2/2005 | Seipel et al. |
| 2005/0143268 | A1 | 6/2005 | Midha |
| 2005/0181067 | A1 | 8/2005 | Yokoyama et al. |
| 2005/0202984 | A1 | 9/2005 | Schwartz et al. |
| 2006/0024256 | A1 | 2/2006 | Wells |
| 2006/0024381 | A1 | 2/2006 | Schwartz et al. |
| 2006/0045861 | A1 | 3/2006 | Bejger et al. |
| 2006/0251605 | A1 | 11/2006 | Belmar |
| 2006/0269501 | A1 | 11/2006 | Johnson et al. |
| 2006/0269502 | A1 | 11/2006 | Johnson et al. |
| 2007/0110696 | A1 | 5/2007 | Johnson et al. |
| 2007/0110700 | A1 | 5/2007 | Wells |
| 2007/0128147 | A1 | 6/2007 | Schwartz et al. |
| 2008/0152611 | A1 | 6/2008 | Wells et al. |
| 2008/0187507 | A1 | 8/2008 | Johnson et al. |

FOREIGN PATENT DOCUMENTS

| | | | |
|---|---|---|---|
| DE | 10005162 | A1 | 8/2001 |
| EP | 0037318 | A1 | 10/1981 |
| EP | 0077630 | | 4/1985 |
| EP | 0555690 | | 8/1993 |
| EP | 0627216 | A2 | 12/1994 |
| EP | 0976393 | A1 | 2/2000 |
| EP | 1123693 | | 2/2000 |
| EP | 1082086 | | 3/2001 |
| EP | 1123693 | A2 | 8/2001 |
| EP | 1161869 | | 12/2001 |
| FR | 2478467 | | 9/1981 |
| FR | 2593801 | | 8/1987 |
| GB | 849433 | | 9/1960 |
| GB | 2177108 | | 1/1987 |
| GB | 2177108 | A | 1/1987 |
| JP | 52/092881 | | 8/1977 |
| JP | 6134227 | | 5/1994 |
| JP | 7118103 | | 5/1995 |
| JP | 2000-103724 | * | 4/2000 |
| JP | 2000/103724 | | 4/2000 |
| JP | 2001181145 | A2 | 7/2001 |
| JP | 2001311099 | A2 | 11/2001 |
| JP | 2002/104940 | | 4/2002 |
| JP | 2002-104940 | | 10/2002 |
| JP | 2004/262805 | | 9/2004 |
| JP | 2004-262805 | A1 | 9/2004 |
| JP | 2004/292387 | | 10/2004 |
| JP | 2004-292387 | A | 10/2004 |
| JP | 2004/292390 | | 10/2004 |
| JP | 2004-292390 | | 10/2004 |
| JP | 2004/307463 | | 11/2004 |
| JP | 2004-307463 | A | 11/2004 |
| JP | 2005/022983 | | 1/2005 |
| JP | 2005-022983 | A | 1/2005 |
| JP | 2005/187342 | A | 7/2005 |
| JP | 2006063044 | A2 | 3/2006 |
| WO | WO-93/08787 | A2 | 5/1993 |
| WO | WO 9308787 | | 5/1993 |
| WO | WO 9410973 | | 5/1994 |
| WO | WO-95/01152 | A1 | 1/1995 |
| WO | WO 9501152 | | 1/1995 |
| WO | WO 9625913 | | 8/1996 |
| WO | WO-97/14396 | A1 | 4/1997 |
| WO | WO 9714396 | | 4/1997 |
| WO | WO 9847372 | | 10/1998 |
| WO | WO 9938475 | | 8/1999 |
| WO | WO-99/51199 | A1 | 10/1999 |
| WO | WO 9951199 | | 10/1999 |
| WO | WO 9959540 | | 11/1999 |
| WO | WO 00/66081 | * | 11/2000 |
| WO | WO 0066081 | | 11/2000 |
| WO | WO-01/00149 | A1 | 1/2001 |
| WO | WO 0100149 | | 1/2001 |
| WO | WO 01/17492 | * | 3/2001 |
| WO | WO 0117492 | | 3/2001 |
| WO | WO-01/39735 | A1 | 6/2001 |
| WO | WO 0139735 | | 6/2001 |
| WO | WO-01/78657 | A | 10/2001 |
| WO | WO 0178657 | | 10/2001 |
| WO | WO-02/22091 | A2 | 3/2002 |
| WO | WO 0219977 | | 3/2002 |

| | | |
|---|---|---|
| WO | WO 0222091 | 3/2002 |
| WO | WO 0232361 | 4/2002 |
| WO | WO 02076422 | 10/2002 |
| WO | WO 02080943 | 10/2002 |
| WO | WO 03032934 | 4/2003 |
| WO | WO-03/101418 A | 12/2003 |
| WO | WO 03101418 | 12/2003 |
| WO | WO 2005/048959 | 6/2005 |
| WO | WO-2005/048959 A | 6/2005 |

OTHER PUBLICATIONS

Savic, Snezana et al, "Colloidal Microstructure of binary systems and model creams stabilized with an alkylpolyglucoside non-ionic emulsifier", *Colloid Polymer Science, Springer-Verlag*, Sep. 28, 2004, p. 439-451, fig 5, vol. 283, XP002413673.

Barry & Rowe, *The Characterization by Small Angle X-Ray Scattering of a Gel with a Lamellar Structure*, International Journal of Pharmaceuticals, 1989.

Barry & Saunders, *Kinetics of Structure Build-up in Self Bodied Emulsions Stabalized by Mixed Emulsifiers*, Journal of Colloid Science, vol. 41, 1972.

Barry, B.W., Structure and Rheology of Emulsions Stabalized by Mixed Emulsifiers, British Society of Rheology, 1970.

Benton et al, Phase Behavior and Network Formation in a Cationic Surfactant-Fatty Alcohol System, JAOCS, vol. 64, 1987.

Burgess, J.D., Practical Analysis of Complex Coacervate Systems, Journal of Colloid Science, vol. 140, 1990.

CTFA Cosmetic Ingredient Dictionary, 1982, 3rd Edition, The Cosmetic, Toiletry & Fragrance Association, Inc., Washington, DC (*book not included*).

1—Eccleston, G.M., *Application of Emulsion Stability Theories to Mobile and Semisolid o/w Emulsions*, Cosmetics Magazine, vol. 101, 1986.

2—Eccleston, G.M., *Application of Emulsion Theory to Complex and Real Systems*, International Journal of Cosmetic Science, 1985.

3—Eccleston, G.M., *Formulating Cosmetic Emulsions*, Cosmetics Magazine, vol. 112, 1997.

4—Eccleston, G.M., *Functions of Mixed Emulsifiers and Emulsifying Waxes in Dermatological Lotions and Creams*, Colloids and Surfaces, vol. 123, 1997.

5—Eccleston, G.M., *Microstructural Changes During Storage of Cetostearyl Alcohol/Polyoxyethylene Alkyl Ether Surfactants*, University of Strathclyde, 1988.

6—Eccleston, G.M., *Multiple Phase Oil and Water Emulsions*, Journal of Cosmetic Chemists, 1990.

7—Eccleston, G.M., *Structure and Rheology of Semisolid o/w Creams Containing Cetyl Alcohol/Non-ionic Surfactant Mixed Emulsifier and Different Polymers*, International Journal of Cosmetic Science, 2004.

8—Eccleston, G.M., Synchrotron X-ray Investigations into the Lamellar Gel Phase Formed in Creams Prepared with Fatty Alcohols, International Journal of Pharmaceuticals, 2000.

9—Eccleston, G.M., The Influence of Fatty Alcohols on the Structure and Stability of Creams Preapred with Fatty Alcohols, International Journal of Cosmetic Science, 1982.

Encyclopedia of Polymer Science and Engineering, John Wiley & Sons, vol. 15, 1989 (book not included).

Griffin, W.C., Calculation of HLB Values of Non-Ionic Surfactants, Journal of the Society of Cosmetic Chemists; 1954. vol. 5, pp. 249-235.

Korhonen et al, Rheological Properties of Three Component Creams Containing Sorbitan Monoesters as Surfactants, International Journal of Pharmaceuticals, 2002.

Louden et al, A Preliminary Examination of the Structure of Gels and Emulsions Containing Cetostearyl Alcohol, International Journal of Pharmaceuticals, 1985.

McCutcheon, Emulsifiers and Detergents, MC Pub Company, 1989 (book not included).

Noll, W., Chemistry and Technology of Silicones, Academic Press, 1968 (book not included).

Patel et al, Properties of Cetrimide / Cetostearyl Alcohol Ternary Gels; Preparation Effects, International Journal of Pharmaceuticals, 1985.

Savic et al, *Colloidal Microstructure of Binary Systems and Model Creams Stablized with an Alkylpolyglucoside Emulsifier*, Colloid Polymer Science, vol. 283, 2004.

Saxton, C., *Antiplaque Effects and Mode of Action of a Combination of Zinc Citrate and a Nonionic Antimicrobial Agent*, Scandinavian Journal, vol. 96, 1988.

Suzuki et al, *Secondary Droplet Emulsion: Mechanism & Effects of Liquid Crystal Formation in o/w Emulsion*, Journal of Dispersion Science, 1984.

Van Cutsem, Journal of the American Academy of Dermatology, XP-002288119, 1998.

Van Oss, C.J., Coacervation, Complex Coacervation and Flocculation, Journal of Dispersion Science, vol. 9, 1989.

Yoon et al, *A Study of Gel Structure in the Nonionic Surfactant / Cetostearyl Alcohol / Water Ternary Systems by Differential Scanning Calorimeter*, Journal of Dispersion Science, 1999.

* cited by examiner

SHAMPOO CONTAINING A GEL NETWORK AND A NON-GUAR GALACTOMANNAN POLYMER DERIVATIVE

CROSS REFERENCE TO RELATED APPLICATION

This application is a continuation-in-part of prior U.S. application Ser. No. 11/228,770, filed on Sep. 16, 2005; which is a continuation-in-part of prior U.S. application Ser. No. 10/454,433, now granted as U.S. Pat. No. 7,303,744, filed on Jun. 4, 2003; which claims the benefit of U.S. Provisional Application Ser. No. 60/385,641, filed on Jun. 4, 2002.

FIELD OF THE INVENTION

The present invention relates to a hair cleansing and conditioning shampoo containing the combination of a non-guar galactomannan polymer derivative and a gel network comprising a fatty amphiphile.

BACKGROUND OF THE INVENTION

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair."

A variety of approaches have been developed to alleviate these after-shampoo problems. These approaches range from post-shampoo application of hair conditioners such as leave-on and rinse-off products, to hair conditioning shampoos which attempt to both cleanse and condition the hair from a single product.

Coacervate formation in a shampoo composition is known to be advantageous for providing conditioning benefits to the hair. The use of cationic polymers to form coacervate is known in the art, such as in PCT publications WO 93/08787 and WO 95/01152. Commonly used cationic deposition polymers include natural polymers, such as guar gum polymers that have been modified with cationic substituents. Guar gum polymers are galactomannans containing two mannose monomers with a glycoside linkage and one galactose monomer attached to a hydroxyl group of the mannose monomers (i.e., guar gum polymers have a mannose to galactose ratio of 2:1). The selection of a cationic guar deposition polymer with sufficient charge density and molecular weight results in sufficient deposition of conditioning agents.

However, to achieve this sufficient deposition of conditioning agents in shampoo or body wash compositions using a cationic guar polymer, a relatively high level of such cationic guar polymer generally must be deposited on the hair or skin. Moreover, the cost of such cationic guar polymer is relatively high. As a result, incorporation of cationic guar polymer can add to the manufacturing costs of such shampoo compositions. Additionally, these shampoo compositions typically are good for delivering wet hair conditioning, but are not capable of delivering satisfactory dry hair smooth feel.

Based on the foregoing, there is a need for a conditioning shampoo which can provide improved conditioning benefit for dry hair, while not interfering with the cleansing efficacy, nor providing negative feel to the hair when it is dried. Specifically, there is a need to provide long lasting moisturized feel, smooth feel, and manageability control to the hair when the hair is dried, yet not leave the hair feeling greasy, as well as to provide softness and ease of combing when the hair is wet.

SUMMARY OF THE INVENTION

The present invention is directed to a shampoo composition comprising: (a) from about 5% to about 50% of one or more detersive surfactants, by weight of the shampoo composition; (b) a dispersed gel network phase comprising: (i) at least about 0.05% of one or more fatty amphiphiles, by weight of the shampoo composition; (ii) at least about 0.01% of one or more secondary surfactants, by weight of the shampoo composition; and (iii) water; (c) at least about 0.05%, by weight of the shampoo composition, of a galactomannan polymer derivative with a net positive charge and having a mannose to galactose ratio of greater than 2:1 on a monomer to monomer basis, wherein the galactomannan polymer derivative has: (i) a molecular weight from about 1,000 to about 10,000,000; and (ii) a cationic charge density from about 0.7 meq/g to about 7 meq/g; and (d) at least about 20% of an aqueous carrier, by weight of the shampoo composition.

The present invention is further directed to a method of using the shampoo composition described above.

These and other features, aspects, and advantages of the present invention will become evident to those skilled in the art from a reading of the present disclosure.

DETAILED DESCRIPTION OF THE INVENTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt.%" herein.

All molecular weights as used herein are weight average molecular weights expressed as grams/mole, unless otherwise specified.

The term "charge density", as used herein, refers to the ratio of the number of positive charges on a polymer to the molecular weight of said polymer.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "polymer" as used herein shall include materials whether made by polymerization of one type of monomer or made by two (i.e., copolymers) or more types of monomers.

The term "shampoo" as used herein means a composition for cleansing and conditioning hair or skin, including scalp, face, and body.

The term "suitable for application to human hair" as used herein means that the compositions or components thereof so described are suitable for use in contact with human hair and the scalp and skin without undue toxicity, incompatibility, instability, allergic response, and the like.

The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

The shampoo compositions of the present invention comprise one or more detersive surfactants, a dispersed gel network phase, a non-guar galactomannan polymer derivative, and an aqueous carrier. Each of these essential components, as well as preferred or optional components, is described in detail hereinafter.

A. Detersive Surfactant

The shampoo compositions of the present invention comprise one or more detersive surfactants. The detersive surfactant component is included in shampoo compositions of the present invention to provide cleansing performance. The detersive surfactant may be selected from anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the composition herein include those which are known for use in hair care or other personal care cleansing compositions. The concentration of the anionic surfactant component in the composition should be sufficient to provide the desired cleaning and lather performance, and generally range from about 5% to about 50%, preferably from about 8% to about 30%, more preferably from about 10% to about 25%, even more preferably from about 12% to about 22%, by weight of the composition.

Suitable zwitterionic or amphoteric detersive surfactants for use in the composition herein include those which are known for use in hair care or other personal cleansing compositions. Concentration of such amphoteric detersive surfactants preferably ranges from about 0.5% to about 20%, preferably from about 1% to about 10%. Non-limiting examples of suitable zwitterionic or amphoteric surfactants are described in U.S. Pat. Nos. 5,104,646 and 5,106,609, both to Bolich Jr. et al.

The compositions of the present invention may further comprise additional surfactants for use in combination with the anionic detersive surfactant component described hereinbefore. Suitable additional surfactants include cationic and nonionic surfactants.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

B. Dispersed Gel Network Phase

The shampoo compositions of the present invention comprise a dispersed gel network phase comprising a fatty amphiphile. The gel network phase is included in shampoo compositions of the present invention to provide conditioning benefits. As used herein, the term "gel network" refers to a lamellar or vesicular solid crystalline phase which comprises at least one fatty amphiphile as specified below, at least one secondary surfactant as specified below, and water or other suitable solvents. The lamellar or vesicular phase comprises bi-layers made up of a first layer comprising the fatty amphiphile and the secondary surfactant and alternating with a second layer comprising the water or other suitable solvent. The term "solid crystalline", as used herein, refers to the structure of the lamellar or vesicular phase which forms at a temperature below the melt transition temperature (i.e., the chain melt temperature) of the layer in the gel network comprising the one or more fatty amphiphiles, the melt transition temperature being at least about 27° C. The melt transition temperature may be measured by differential scanning calorimetry, a method of which is described in the Examples below.

Gel networks which comprise, for example, fatty alcohols have been used for years in cosmetic creams and hair conditioners. Such cosmetic creams and hair conditioners, however, typically contain very low amounts, if any, of detersive surfactant. Thus, such known products do not provide a combination of cleansing and conditioning to the hair or skin.

Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M. Eccleston, "The Microstructure of Semisolid Creams", *Pharmacy International*, Vol. 7, 63-70 (1986).

In an embodiment of the present invention, the dispersed gel network phase is pre-formed. The term "pre-formed", as used herein, means that at least fifty percent of the mixture of the fatty amphiphile, secondary surfactant, and water or other suitable solvent is substantially a solid crystalline phase when added to the other components of the shampoo composition.

According to this embodiment of the present invention, the gel network component of the present invention is prepared as a separate pre-mix, which, after being cooled, is subsequently incorporated with the detersive surfactant and the other components of the shampoo composition. Preparation of the gel network component is discussed in more detail below in the section entitled Process of Making a Shampoo Composition, as well as in the Examples.

The cooled and pre-formed gel network component subsequently is added to the other components of the shampoo composition, including the detersive surfactant component. While not intending to be limited by theory, it is believed that incorporation of the cooled and pre-formed gel network component with the detersive surfactant and other components of the shampoo composition allows the formation of a substantially equilibrated lamellar dispersion ("ELD") in the final shampoo composition. The ELD is a dispersed lamellar or vesicular phase resulting from the pre-formed gel network component substantially equilibrating with the detersive surfactants, water, and other optional components, such as salts, which may be present in the shampoo composition. This equilibration occurs upon incorporation of the pre-formed gel network component with the other components of the shampoo composition and is effectively complete within about 24 hours after making. Shampoo compositions in which the ELD is formed provide hair with improved wet and dry conditioning benefits. Further, the ELD does not form if the components which comprise the gel network component (i.e., the fatty amphiphile and the secondary surfactant combined with water) are added as individual components together with the other components of the shampoo composition in one mixing step, and not as a separate cooled pre-formed gel network component.

As described above, the ELD is formed by the incorporation of the cooled and pre-formed gel network component with the detersive surfactant and other components of the shampoo composition. While the ELD and the pre-formed gel network component both comprise fatty amphiphile, secondary surfactant, and water together in the form of a lamellar or vesicular solid crystalline phase, differences exist between certain physical properties of the ELD compared with those of the pre-formed gel network component. Prior to incorporation with the detersive surfactant and other components of the shampoo composition, the pre-formed gel network component consists essentially of fatty amphiphile, secondary surfactant, and water. Upon incorporation, the lamellar structure of the gel network, acting as a template, is swelled by and equilibrates with the detersive surfactant and other components of the shampoo composition, such as salts and perfumes. Thus, it is believed that these differences in certain physical properties between the pre-formed gel network component and the ELD are consistent with the migration of, for example, the detersive surfactant, salts, and perfumes, into the gel network phase.

The presence of the gel network in the pre-mix and in the final shampoo composition in the form of the ELD can be confirmed by means known to one of skill in the art, such as X-ray analysis, optical microscopy, electron microscopy, and differential scanning calorimetry. Methods of X-ray analysis and differential scanning calorimetry are described in U.S. 2006/0024256 A1.

In one embodiment of the present invention, the scale size of the dispersed gel network phase in the shampoo composition (i.e., the ELD) ranges from about 10 nm to about 500 nm. In another embodiment, the scale size of the dispersed gel network phase in the shampoo composition ranges from about 0.5 µm to about 10 µm. In yet another embodiment, the scale size of the dispersed gel network phase in the shampoo composition ranges from about 10 µm to about 150 µm.

The scale size distribution of the dispersed gel network phase in the shampoo composition may be measured with a laser light scattering technique, using a Horiba model LA 910 Laser Scattering Particle Size Distribution Analyzer (Horiba Instruments, Inc. Irvine Calif., USA). The scale size distribution in a shampoo composition of the present invention may be measured by combining 1.75 g of the shampoo composition with 30 mL of 3% $NH_4Cl$, 20 mL of 2% $Na_2HPO_4.7H_2O$, and 10 mL of 1% laureth-7 to form a mixture. This mixture is then stirred for 5 minutes. As appropriate for the individual Horiba instrument being used, samples in the range of 1 to 40 mL are taken and then injected into the Horiba instrument, which contains 75 mL of 3% $NH_4Cl$, 50 mL of 2% $Na_2HPO_4.7H_2O$, and 25 mL of 1% laureth-7, until the Horiba instrument reading is between 88-92% T, which is needed for the scale size measurement. Once this is achieved, a measurement is taken after 2 minutes of circulation through the Horiba instrument to provide the scale size measurement. A subsequent measurement is taken using a sample of the shampoo composition which has been heated above the melt transition temperature of all fatty materials present in the shampoo composition, such that the gel network component is melted. This subsequent measurement allows a scale size distribution to be taken of all of the remaining materials in the shampoo, which then can be compared to the scale size distribution of the first sample and assist in the analysis.

The shampoo composition of the present invention comprise a gel network in an amount greater than about 0.1%, preferably from about 1% to about 60%, and more preferably from about 5% to about 40%, by weight of the shampoo composition.

1. Fatty Amlphiphile

The gel network component of the present invention comprises at least one fatty amphiphile. As used herein, "fatty amphiphile" refers to a compound having a hydrophobic tail group and a hydrophilic head group which does not make the compound water soluble, wherein the compound also has a net neutral charge at the pH of the shampoo composition.

The fatty amphiphile of the present invention may be characterized as a compound having a Hydrophilic-Lipophilic Balance ("HLB") of 6 or less. The HLB, as used herein, is the standard HLB according to Griffin, J. Soc. Cosm. Chem., vol. 5, 249 (1954).

According to the present invention, suitable fatty amphiphiles, or suitable mixtures of two or more fatty amphiphiles, have a melting point of at least about 27° C. The melting point, as used herein, may be measured by a standard melting point method as described in U.S. Pharmacopeia, USP-NF General Chapter <741> "Melting range or temperature". The melting point of a mixture of two or more materials is determined by mixing the two or more materials at a temperature above the respective melt points and then allowing the mixture to cool. If the resulting composite is a homogeneous solid below about 27° C., then the mixture has a suitable melting point for use in the present invention. A mixture of two or more fatty amphiphiles, wherein the mixture comprises at least one fatty amphiphile having an individual melting point of less than about 27° C., still is suitable for use in the present invention provided that the composite melting point of the mixture is at least about 27° C.

According to the present invention, suitable fatty amphiphiles have a hydrophobic tail group. This hydrophobic tail group may be an alkyl, alkenyl (containing up to 3 double bonds), alkyl aromatic, or branched alkyl group with a length of from about 12 to about 70 carbon atoms, and in one embodiment from about 16 to about 60 carbon atoms, and in another embodiment from about 16 to about 50 carbon atoms, and in yet another embodiment from about 16 to about 40 carbon atoms, and in even yet another embodiment from about 16 to about 22 carbon atoms, and in another embodiment from about 18 to 22 carbon atoms. Non-limiting examples of alkyl, alkenyl, or branched alkyl groups suitable for the fatty amphiphiles of the present invention include lauryl, tridecyl, myristyl, pentadecyl, cetyl, heptadecyl, stearyl, arachidyl, behenyl, undecylenyl, palmitoleyl, oleyl, palmoleyl, linoleyl, linolenyl, arahchidonyl, elaidyl, elaeostearyl, erucyl, isolauryl, isotridecyl, isomyristal, isopentadecyl, petroselinyl, isocetyl, isoheptadecyl, isostearyl, isoarachidyl, isobehnyl, gadoleyl, brassidyl, and technical-grade mixture thereof.

Suitable fatty amphiphiles of the present invention also have a hydrophilic head group which does not make the compound water soluble, such as in compounds having an HLB of 6 or less. Non-limiting examples of classes of compounds having such a hydrophilic head group include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, fatty phosphate esters, and phospholipids. For additional discussion of fatty amphiphiles which are suitable for use in the present invention, see U.S. 2006/0024256 A1.

To form the gel network component of the present invention, individual fatty amphiphile compounds or combinations of two or more different fatty amphiphile compounds may be selected.

The shampoo compositions of the present invention comprise fatty amphiphile as part of the pre-formed dispersed gel network phase in an amount from about 0.05% to about 14%, preferably from about 0.5% to about 10%, and more preferably from about 1% to about 8%, by weight of the shampoo composition.

In an embodiment of the present invention, the weight ratio of the fatty amphiphile to the secondary surfactant in the gel network component is greater than about 1:9, preferably greater than about 1:5 to about 100:1, more preferably greater than about 1:1 to about 50:1, and even more preferably greater than about 2:1 to about 10:1.

2. Secondary Surfactant

The gel network component of the present invention also comprises a secondary surfactant. As used herein, "secondary surfactant" refers to one or more surfactants which are combined with the fatty amphiphile and water to form the gel network of the present invention as a pre-mix separate from the other components of the shampoo composition. The secondary surfactant is separate from and in addition to the detersive surfactant component of the shampoo composition. However, the secondary surfactant may be the same or different type of surfactant or surfactants as that or those selected for the detersive surfactant component described above.

The shampoo compositions of the present invention comprise secondary surfactant as part of the pre-formed dispersed gel network phase in an amount from about 0.01% to about 15%, preferably from about 0.1% to about 10%, and more preferably from about 0.3% to about 5%, by weight of the shampoo composition.

Suitable secondary surfactants include anionic, zwitterionic, amphoteric, cationic, and nonionic surfactants. Preferably, the secondary surfactant is selected from anionic, cationic, and nonionic surfactants, and mixtures thereof. For additional discussion of secondary surfactants which are suitable for use in the present invention, see U.S. 2006/0024256 A1.

Additionally, in an embodiment of the present invention, certain secondary surfactants which have a hydrophobic tail group with a chain length of from about 16 to about 22 carbon atoms may be selected to contribute to obtaining a melt transition temperature of at least about 38° C. for the resulting dispersed gel network phase. For such secondary surfactants, the hydrophobic tail group may be alkyl, alkenyl (containing up to 3 double bonds), alkyl aromatic, or branched alkyl. In such an embodiment, it is preferred that the secondary surfactant is present in the gel network component relative to the fatty amphiphile at a weight ratio from about 1:5 to about 5:1.

Mixtures of more than one surfactant of the above specified types may be used for the secondary surfactant of the present invention.

3. Water or Suitable Solvents

The gel network component of the present invention also comprises water or suitable solvents. The water or suitable solvent and the secondary surfactant together contribute to the swelling of the fatty amphiphile. This, in turn, leads to the formation and the stability of the gel network. As used herein, the term "suitable solvent" refers to any solvent which can be used in the place of or in combination with water in the formation of the gel network of the present invention.

The shampoo compositions of the present invention comprise water or suitable solvents as part of the pre-formed dispersed gel network phase in an amount suitable to achieve a gel network when combined with fatty amphiphile and secondary surfactant according to the present invention.

In a preferred embodiment, the shampoo compositions of the present invention comprise as part of the pre-formed dispersed gel network phase at least about 0.05% of water or a suitable solvent, by weight of the shampoo composition.

In another embodiment of the present invention, the shampoo compositions comprise water or a suitable solvent as part of the pre-formed dispersed gel network phase is an amount relative to the amount of fatty amphiphile at a weight ratio of at least about 1:1.

C. Galactomannan Polymer Derivative

The shampoo compositions of the present invention comprise galactomannan polymer derivatives with a net positive charge and having a mannose to galactose ratio of greater than 2:1 on a monomer to monomer basis. Included within galactomannan polymer derivatives with a net positive charge are "cationic galactomannan", which refers to a galactomannan polymer to which a cationic group is added, and "amphoteric galactomannan", which refers to a galactomannan polymer to which a cationic group and an anionic group are added but such that the polymer has a net positive charge. These galactomannan polymer derivatives are included in the shampoo compositions of the present invention to enhance effective deposition of the dispersed gel network phase on hair and/or skin.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of $\beta$ (1-4) glycosidic linkages. The galactose branching arises by way of an $\alpha$ (1-6) linkage. The ratio of mannose monomers to galactose monomers varies according to the species of the plant and also is affected by climate. Guar is an example of one type of a galactomannan polymer, specifically having a mannose to galactose ratio of 2 monomers of mannose to 1 monomer of galactose.

Galactomannan polymers of the present invention have a ratio of mannose to galactose of greater than 2:1 on a monomer to monomer basis (i.e., non-guar galactomannan polymers). Preferably, the ratio of mannose to galactose is greater than about 3:1, and more preferably the ratio of mannose to galactose is greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to tara gum (3 parts mannose/1 part galactose), locust bean or carob (4 parts mannose/1 part galactose), and cassia gum (5 parts mannose/1 part galactose).

In one embodiment of the present invention, a preferred gum for use in preparing the non-guar galactomannan polymer derivatives is cassia gum. Cassia gum derivatives can provide at least comparable deposition of conditioning agents on hair as guar gum derivatives, yet cassia gum derivatives generally can be obtained commercially at a relatively lower cost than guar gum derivatives.

The galactomannan polymer derivatives for use in the personal care compositions of the present invention have a molecular weight from about 1,000 to about 10,000,000. In one embodiment of the present invention, the galactomannan polymer derivatives have a molecular weight from about 5,000 to about 3,000,000. As used herein, the term "molecular weight" refers to the weight average molecular weight. The weight average molecular weight may be measured by gel permeation chromatography.

The shampoo compositions of the present invention include galactomannan polymer derivatives which have a cationic charge density from about 0.7 meq/g to about 7 meq/g. In one embodiment of the present invention, the galactomannan polymer derivatives have a charge density from about 0.9 meq/g to about 7 meq/g. In another embodiment of the present invention, the galactomannan polymer derivatives have a charge density from about 0.7 meq/g to about 1.0 meq/g. In yet another embodiment, the galactomannan polymer derivatives have a charge density from about 1.1 meq/g to about 3.5 meq/g. The degree of substitution of the cationic groups onto the galactomannan structure should be sufficient to provide the requisite cationic charge density.

In one embodiment of the present invention, the galactomannan polymer derivative is a cationic derivative of the non-guar galactomannan polymer, which is obtained by reaction between the hydroxyl groups of the galactomannan polymer and reactive quaternary ammonium compounds. Suitable quaternary ammonium compounds for use in forming the cationic galactomannan polymer derivatives include those conforming to the general formula:

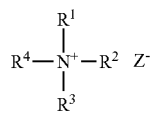

wherein where $R^1$, $R^2$ and $R^3$ are methyl or ethyl groups; $R^4$ is either an epoxyalkyl group of the general formula:

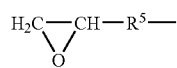

or $R^4$ is a halohydrin group of the general formula:

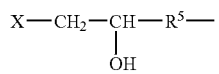

wherein $R^5$ is a $C_1$ to $C_3$ alkylene; X is chlorine or bromine, and Z is an anion such as $Cl^-$, $Br^-$, $I^-$ or $HSO_4^-$.

Cationic non-guar galactomannan polymer derivatives formed from the reagents described above are represented by the general formula:

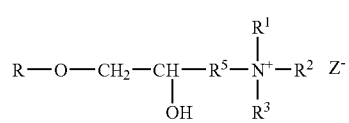

wherein R is the gum. Preferably, the cationic galactomannan derivative is a gum hydroxypropyltrimethylammonium chloride, which can be more specifically represented by the general formula:

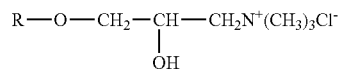

The shampoo compositions of the present invention comprise galactomannan polymer derivatives at a range of about 0.01% to about 10%, and more preferably from about 0.05% to about 5%, by weight of the composition.

D. Aqueous Carrier

The shampoo compositions of the present invention comprise an aqueous carrier. Typically, the compositions of the present invention are in the form of pourable liquids (under ambient conditions). The compositions, therefore, comprise an aqueous carrier at a level of from about 20% to about 95%, preferably from about 60% to about 85%, by weight of the compositions. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

E. Additional Components

The compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the compositions.

Non-limiting examples of optional components for use in the composition include cationic polymers, conditioning agents (hydrocarbon oils, fatty esters, silicones), anti-dandruff agents, suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

1. Additional Deposition Aid

The shampoo compositions of the present invention may include a deposition aid in addition to the non-guar galactomannan polymer derivative of the present invention. The additional deposition aid is included to further enhance deposition of the gel network component. The deposition aid can comprise any material that enhances the deposition of the gel network from the shampoo onto the hair and/or scalp.

The concentration of the deposition aid in the shampoo composition should be sufficient to effectively enhance the deposition of the gel network component and ranges from about 0.05% to about 5%, preferably from about 0.075% to about 2.5%, more preferably from about 0.1% to about 1.0%, by weight of the shampoo composition.

In one embodiment of the present invention, the deposition aid is an additional cationic polymer, other than the non-guar galactomannan polymer of the present invention. Preferred cationic polymers will have cationic charge densities of at least about 0.7 meq/g, preferably at least about 1.2 meq/g, more preferably at least about 1.5 meq/g, but also preferably less than about 7 meq/g, more preferably less than about 5 meq/g, at the pH of intended use of the composition. The pH will generally range from about pH 3 to about pH 9, preferably between about pH 4 and about pH 8. The average molecular weight of such suitable cationic polymers will generally be between about 10,000 and 10 million, preferably between about 50,000 and about 5 million, more preferably between about 100,000 and about 3 million.

Suitable cationic polymers for use in the composition include polysaccharide polymers, such as cationic cellulose derivatives and cationic starch derivatives, such as salts of hydroxyethyl cellulose reacted with trimethyl ammonium substituted epoxide. Other suitable cationic polymers include cationic guar gum derivatives, such as guar hydroxypropyltrimonium chloride.

2. Dispersed Particles

The composition of the present invention may include dispersed particles. Particles useful in the present invention can be inorganic, synthetic, or semi-synthetic in origin. If present in the compositions of the present invention, dispersed particles are incorporated in an amount from about 0.025% to about 20%, preferably from about 0.05% to about 10%, more preferably from about 0.1% to about 5%, even more preferably from about 0.25% to about 3%, and yet more preferably from about 0.5% to about 2%, by weight of the composition.

3. Nonionic Polymers

Polyalkylene glycols having a molecular weight of more than about 1000 are useful herein. Useful are those having the following general formula:

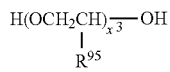

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR. N-3000 available from Union Carbide).

4. Conditioning Agents

The compositions of the present invention may also comprise one or more conditioning agents which are in addition to the dispersed gel network phase. Conditioning agents include materials which are used to give a particular conditioning benefit to hair and/or skin. The conditioning agents useful in the compositions of the present invention typically comprise a water-insoluble, water-dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

In one embodiment, the shampoo composition of the present invention further comprises a non-volatile silicone oil. For an opaque composition embodiment, the shampoo composition comprises a non-volatile silicone oil having a particle size as measured in the shampoo composition from about 1 μm to about 50 μm. In an embodiment of the present invention for small particle application to the hair, the shampoo composition comprises a non-volatile silicone oil having a particle size as measured in the shampoo composition from about 100 nm to about 1 μm. For a substantially clear composition embodiment, the shampoo composition comprises a non-volatile silicone oil having a particle size as measured in the shampoo composition of less than about 100 nm.

When present, the one or more conditioning agents are in an amount from about 0.01% to about 10%, preferably from about 0.1% to about 8%, more preferably from about 0.2% to about 4%, by weight of the composition.

The conditioning agents may be present in the dispersed gel network phase or may be added to the final shampoo composition as a separate component such that they are present primarily in the continuous phase of the shampoo.

5. Anti-Dandruff Actives

The compositions of the present invention may also contain an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the essential components of the composition, and should not otherwise unduly impair product stability, aesthetics or performance.

When present in the composition, the anti-dandruff active is included in an amount from about 0.01% to about 5%, preferably from about 0.1% to about 3%, and more preferably from about 0.3% to about 2%, by weight of the composition.

6. Humectants

The compositions of the present invention may contain a humectant. The humectants herein are selected from the group consisting of polyhydric alcohols, water soluble alkoxylated nonionic polymers, and mixtures thereof. The humectants, when used herein, are preferably present in an amount by weight of the composition from about 0.1% to about 20%, more preferably from about 0.5% to about 5%.

7. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, preferably from about 0.3% to about 5.0%, by weight of the composition.

Suspending agents useful herein include crystalline suspending agents which can be categorized as acyl derivatives, long chain amine oxides, and mixtures thereof. These suspending agents are described in U.S. Pat. No. 4,741,855. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate.

8. Other Optional Components

The compositions of the present invention may contain other optional components. Optional components may be present in the dispersed gel network phase or may be added to the final shampoo composition as separate components.

For example, the compositions of the present invention may contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts. The compositions of present invention may further comprise materials useful for hair loss prevention and hair growth stimulants or agents.

Any other suitable optional component can also be included in the composition of the present invention, such as those ingredients that are conventionally used in given product types. The CTFA Cosmetic Ingredient Handbook, Tenth Edition (2004), published by the Cosmetic, Toiletry, and Fragrance Association, Inc., Washington, D.C., describes a wide variety of nonlimiting materials that can be added to the composition herein. Examples of these ingredient classes include, but are not limited to: abrasives, absorbents, aesthetic components such as perfumes and fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antibacterial agents, antifungal agents, antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching and lightening agents, (e.g., hydroquinone, kojic acid, ascorbic acid, magnesiuim ascorbyl phosphate, ascorbyl glucoside, pyridoxine), enzymes, coenzymes, skin-conditioning agents (e.g., humectants and occlusive agents), skin soothing and/or healing agents and derivatives (e.g., panthenol, and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, cedrol), thickeners (including a mono- or divalent salt such as sodium chloride), and vitamins, their derivatives, and combinations thereof.

When certain oil-soluble components, such as perfumes and fragrances, amino acids, water-insoluble vitamins, and the like, are present in the dispersed gel network phase, either by incorporating such components directly into the gel network component pre-mix or separately into the shampoo composition and consequently some amount of such components migrate into the dispersed gel network phase during equilibration, they may be effectively deposited on hair and/or skin. To obtain very effective deposition of oil-soluble components on hair and/or skin via their presence in the dispersed gel network phase, oil-soluble component compositions which comprise no less than about 60% of ingredients having a Clog P of about 3 or higher are preferred. For further discussion on Clog P and how to determine its value for a variety of materials, see, for example, U.S. Pat. Nos. 5,849,310 and 5,500,154 as well as EP 1 533 364.

F. Process of Making a Shampoo Composition

An aspect of the invention relates to a process of making a shampoo composition of the present invention. The process of making a shampoo composition comprises (a) combining a fatty amphiphile, a secondary surfactant, and water at a temperature sufficient to allow partitioning of the secondary surfactant and the water into the fatty amphiphile to form a pre-mix; (b) cooling the pre-mix below the chain melt temperature of the fatty amphiphile to form a gel network; (c) adding the gel network to one or more detersive surfactants and an aqueous carrier to form a shampoo composition.

As discussed above, in one embodiment of the present invention, the gel network component is prepared as a separate pre-mix, which, after being cooled, is subsequently incorporated with the other components of the shampoo composition. More specifically, the gel network component of the present invention may be prepared by heating the fatty amphiphile, the secondary surfactant, and water to a level in the range of about 75° C. to about 90° C. and mixing. This mixture is cooled to a level in the range of about 27° C. to about 35° C. by, for example, passing the mixture through a heat exchanger. As a result of this cooling step, at least about fifty percent of the mixture of the fatty amphiphile and the secondary surfactant crystallize to form a crystalline gel network.

Alternative methods of preparing the gel network component include sonication and/or milling of the fatty amphiphile, the secondary surfactant, and water, while these components are heated, to reduce the particle size of the melted fatty amphiphile phase. This results in an increase in surface area of the fatty amphiphile phase, which allows the secondary surfactant and the water to swell the fatty amphiphile phase. Another suitable variation in preparing the gel network includes heating and mixing the fatty amphiphile and the secondary surfactant first, and then adding that mixture to the water.

G. Method of Use

The compositions of the present invention are used in a conventional manner for cleansing and conditioning hair or skin, including scalp, face, and body. Generally, a method of treating hair or skin of the present invention comprises applying the composition of the present invention to the hair or skin. More specifically, an effective amount of the personal care composition is applied to the hair or skin, which has preferably been wetted with water, and then the personal care composition is rinsed off. Such effective amounts generally range from about 1 g to about 50 g, preferably from about 1 g to about 20 g. Application to the hair typically includes working the composition through the hair such that most or all of the hair is contacted with the composition.

The method for treating the hair or skin comprises the steps of: (a) wetting the hair or skin with water; (b) applying an effective amount of the shampoo composition to the hair or skin, and (c) rinsing the applied areas of skin or hair with water. These steps can be repeated as many times as desired to achieve the desired cleansing and conditioning benefit.

In one embodiment, the shampoo composition of the present invention advantageously is used to treat damaged hair. Damaged hair may include hair selected from permed hair, oxidatively colored hair, and mechanically damaged hair.

In another embodiment, the shampoo composition is used to treat skin, such as the scalp, the face, and the body.

The personal care compositions of this invention may be used as liquids, solids, semi-solids, flakes, gels, placed in a pressurized container with a propellant added, or used in a pump spray form. The viscosity of the product may be selected to accommodate the form desired.

NON-LIMITING EXAMPLES

The shampoo compositions illustrated in the following Examples illustrate specific embodiments of the shampoo compositions of the present invention, but are not intended to be limiting thereof. Other modifications can be undertaken by the skilled artisan without departing from the spirit and scope of this invention. These exemplified embodiments of the shampoo composition of the present invention provide enhanced conditioning benefits to the hair.

The shampoo compositions illustrated in the following Examples are prepared by conventional formulation and mixing methods, an example of which is set forth hereinbelow. All exemplified amounts are listed as weight percents and exclude minor materials such as diluents, preservatives, color solutions, imagery ingredients, botanicals, and so forth, unless otherwise specified. All percentages are based on weight unless otherwise specified.

Preparation of the Gel Network Pre-Mix

To prepare the gel network pre-mix, about 20% of the water is heated to about 74° C. and the fatty amphiphile and the secondary surfactant (e.g., Behenyltrimethylammonium chloride (Varisoft BT-85) or Sodium Laureth Sulfate) are added to it. After incorporation, this mixture is passed through a mill and heat exchanger where it is cooled to about 35° C. As a result of this cooling step, the fatty amphiphile, the secondary surfactant, and the water form a crystalline gel network.

For mixtures of different fatty amphiphiles, it may be beneficial to pre-mix the fatty amphiphile materials before incorporation into the water. This can be done by co-melting the different fatty amphiphiles together and utilizing this melt or cooling into a solid phase and incorporating this into the heated water along with the secondary surfactant. Another variation could be to co-melt the one or more fatty amphiphiles and the secondary surfactant before incorporation into the water. Some gel network compositions with chain melt temperatures between about 27° C. to about 35° C. will need to be cooled below 27° C. to ensure the lamellar phase structure is froze.

Gel Network Pre-Mix Examples 1-28

The following Examples illustrate specific embodiments of the gel network pre-mix, prior to its incorporation with the detersive surfactant and other components of the final shampoo composition of the present invention. It is intended that each of the following gel network pre-mix examples could be incorporated as a dispersed phase into a shampoo composition according to the present invention.

| Ingredient | 1 | 2 | 3 | 4 | 5 | 6 | 7 |
|---|---|---|---|---|---|---|---|
| Water | 88.55% | 88.55% | 88.55% | 88.55% | 88.55% | 88.55% | 88.55% |
| Glyceryl palmitate (1) | | | | | | 4.29% | |
| Glyceryl stearate, Glyceryl Stearate Pure (1) | | | | | | 4.29% | |
| Sorbitan tristearate (1) | 8.58% | | | | | | |
| Stearamide MEA-stearate (1) | | 8.58% | | | | | |
| Steareth-2, Volpo S-2 (2) | | | 8.58% | | | | 6.44% |
| Stearic acid, V-1890 (3) | | | | 8.58% | | | 2.14% |
| Sucrose distearate, Crodesta F-10 (2) | | | | | 8.58% | | |
| Behenyltrimethylammonium chloride, Varisoft BT-85 (4) | 2.84% | 2.84% | 2.84% | 2.84% | 2.84% | 2.84% | 2.84% |
| 5-Chloro-2-methyl-4-isothiazolin-3-one, Kathon CG | 0.03% | 0.03% | 0.03% | 0.03% | 0.03% | 0.03% | 0.03% |

| Ingredient | 8 | 9 | 10 | 11 | 12 | 13 | 14 |
|---|---|---|---|---|---|---|---|
| Water | 82.75% | 82.75% | 82.75% | 82.75% | 82.75% | 82.75% | 82.75% |
| PEG-2 Stearate (1) | 8.58% | | | | | | |
| PEG-5 Glyceryl stearate (1) | | 8.58% | | | | | |
| PEG-6 Stearate (1) | | | 8.58% | | | | |
| SEFA Stearate, Sefose-1618H (3) | | | | 8.58% | | | |
| Sorbitan palmitate (1) | | | | | 8.58% | | |
| Sorbitan stearate, Crill 3 NF (2) | | | | | | 8.58% | |
| Sorbitan stearate (1) | | | | | | | 8.58% |
| Sodium laureth-3 sulfate (28% Active) | 8.64% | 8.64% | 8.64% | 8.64% | 8.64% | 8.64% | 8.64% |
| 5-Chloro-2-methyl-4-isothiazolin-3-one, Kathon CG | 0.03% | 0.03% | 0.03% | 0.03% | 0.03% | 0.03% | 0.03% |

| Ingredient | 15 | 16 | 17 | 18 | 19 | 20 | 21 |
|---|---|---|---|---|---|---|---|
| Water | 82.75% | 82.75% | 82.75% | 82.76% | 82.75% | 82.75% | 82.75% |
| Cetyl Alcohol | | | | 3.00% | | | |
| Cocamine oxide | | | | | | | 4.30% |
| Glyceryl distearate (1) | | | | | | 4.30% | |
| Sorbitan tristearate (1) | 8.58% | | | | | | |
| Steary Alcohol | | | | | 5.57% | | |
| Stearamide MEA-stearate (1) | | 8.58% | | | | | |
| Steareth-2, Volpa S-2 (2) | | | 8.58% | | | | |
| Stearic acid, V-1890 (3) | | | | | | 4.28% | |
| Sucrose distearate, Crodesta F-10 (2) | | | | | 8.58% | | 4.28% |
| Sodium laureth-3 sulfate (28% Active) | 8.64% | 8.64% | 8.64% | 8.64% | 8.64% | 8.64% | 8.64% |
| 5-Chloro-2-methyl-4-isothiazolin-3-one, Kathon CG | 0.03% | 0.03% | 0.03% | 0.03% | 0.03% | 0.03% | 0.03% |

| Ingredient | 22 | 23 | 24 | 25 | 26 | 27 | 28 |
|---|---|---|---|---|---|---|---|
| Water | 88.55% | 88.55% | 88.78% | 88.55% | 88.78% | 88.78% | 88.78% |
| Stearyl Alcohol | | 5.57% | | | | 2.48% | 3.21% |
| Cetyl Alcohol | | 3.00% | | | | 2.47% | 1.74% |
| Glyceryl hydroxystearate (1) | | | | | 4.95% | | |
| PEG-2 Stearate (1) | | | | | 4.95% | | |
| Palmitic Acid | 3.00% | | | 5.72% | | | |
| Steareth-2, Volpo S-2 (2) | | | 4.95% | | 4.95% | | |

-continued

| | | | | | | | |
|---|---|---|---|---|---|---|---|
| Stearic acid, V-1890 (3) | 5.57% | | 4.95% | 2.86% | 4.95% | 4.95% | 4.95% |
| Behenyltrimethylammonium chloride, Varisoft BT-85 (2) | 2.85% | 2.85% | 1.29% | 2.84% | 1.29% | 1.29% | 1.29% |
| 5-Chloro-2-methyl-4-isothiazolin-3-one, Kathon CG | 0.03% | 0.03% | 0.03% | 0.03% | 0.03% | 0.03% | 0.03% |

(1) available from A&E Connock
(2) available from Croda Chemicals
(3) available from P&G Chemicals
(4) available Goldschmidt Chemical Preparation of Final Shampoo Compositions To prepare the final shampoo composition, first, a surfactant solution pre-mix is formed. To prepare this surfactant solution pre-mix, about 6% to about 9% of sodium or ammonium laureth-3 sulfate, cationic polymers, and about 0% to about 5% of water are added to a jacketed mix tank and heated to about 74° C. with agitation. To this solution, citric acid, sodium citrate, sodium benzoate, and disodium EDTA are added to the tank and allowed to disperse. Ethylene glycol distearate (EGDS) is then added to the mixing vessel and melted. After the EGDS was well dispersed (e.g., after about 10 minutes), 15 preservative is added and mixed into the surfactant solution. This mixture is passed through a mill and heat exchanger where it is cooled to about 35° C. and collected in a finishing tank. As a result of this cooling step, the EGDS crystallizes to form a waxy crystalline suspension. The mixture of these components is the surfactant solution pre-mix.

Next, the surfactant solution pre-mix and the gel network pre-mix, which is prepared as described above, are mixed together. The remainder of the surfactants, perfume, dimethicone, sodium chloride or ammonium xylene sulfonate for viscosity adjustment, and the remainder of the water are added with ample agitation to ensure a homogeneous mixture. This mixture is the final shampoo composition which comprises as a dispersed phase the gel network pre-mix.

Preferred viscosities of the final shampoo composition according to the present invention range from about 5000 to about 15,000 centipoise at 27° C., as measured by a Wells-Brookfield model RVTDCP viscometer using a CP-41 cone and plate at 2/s at 3 minutes.

The pH may be adjusted as necessary to provide shampoo compositions of the present invention which are suitable for application to human hair, and may vary based on the selection of particular detersive surfactants, fatty amphiphiles, and/or other components.

Shampoo Examples 1-10

The following Examples illustrate specific embodiments of the final shampoo composition of the present invention, which respectively comprise select above-exemplified gel network pre-mixes as a dispersed phase.

| Ingredient | 1 | 2 | 3 | 4 | 5 | 6 | 7 | 8 | 9 | 10 |
|---|---|---|---|---|---|---|---|---|---|---|
| Sodium Laureth Sulfate | 10.00 | 10.00 | 10.00 | 10.00 | 10.00 | 10.00 | 10.00 | 6.00 | 15.00 | 8.5 |
| Sodium Lauryl Sulfate | 1.50 | 1.50 | 1.50 | 1.50 | 1.50 | 1.50 | 6.00 | 10.00 | 5.00 | 3.00 |
| Cocamidopropyl betaine | 2.00 | 2.00 | 2.00 | 2.00 | 2.00 | 2.00 | 2.00 | 2.00 | 2.00 | 2.00 |
| Any one of Gel Networks 1-28 | 27.3 | 13.6 | | | | | 27.3 | 27.3 | 27.3 | 27.3 |
| Gel Network 18 | | | 27.3 | 27.3 | | | | | | |
| Gel Network 22 | | | | | 27.3 | | | | | |
| Gel Network 25 | | | | | | 27.3 | | | | |
| Cationic Galactomannan (1) | 0.4 | 0.4 | 0.4 | 0.4 | | | 0.3 | 0.3 | 0.2 | 0.2 |
| Cationic Galactomannan (2) | | | | | 0.1 | 0.1 | | | 0.2 | |
| Guar Hydroxypropyl trimonium chloride (3) | | | | | | | | 0.1 | | |
| Guar Hydroxypropyl trimonium chloride (4) | | | | | 0.3 | 0.3 | | | | |
| Polyquaterium-10 (5) | | | | | | | 0.1 | | | |
| Dimethicone (6) | 2.00 | 2.00 | 2.00 | 2.00 | 2.00 | 2.00 | | | 2.00 | 2.00 |
| Dimthicone (7) | | | | | | | 1.00 | | | |
| Dimethicone (8) | | | | | | | | 0.5 | | |
| Ethylene Glycol Distearate | 1.5 | 1.5 | 1.5 | 1.5 | 3.0 | 1.5 | 1.5 | 1.5 | 1.5 | 1.5 |
| 5-Chloro-2-methyl-4-isothiazolin-3-one, Kathon CG | 0.0005 | 0.0005 | 0.0005 | 0.0005 | 0.0005 | 0.0005 | 0.0005 | 0.0005 | 0.0005 | 0.0005 |
| Sodium Benzoate | 0.25 | 0.25 | 0.25 | 0.25 | 0.25 | 0.25 | 0.25 | 0.25 | 0.25 | 0.25 |
| Disodium EDTA | 0.13 | 0.13 | 0.13 | 0.13 | 0.13 | 0.13 | 0.13 | 0.13 | 0.13 | 0.13 |
| Perfume | 0.70 | 0.70 | 0.70 | 0.70 | 0.70 | 0.70 | 0.70 | 0.70 | 0.70 | 0.70 |
| Citric Acid/Sodium Citrate Dihydrate | pH QS | pH QS | pH QS | pH QS | pH QS | pH QS | pH QS | pH QS | pH QS | pH QS |
| Sodium Chloride/ | Visc. | Visc. | Visc. | Visc. | Visc. | Visc. | Visc. | Visc. | Visc. | Visc. |

-continued

| Ingredient | 1 | 2 | 3 | 4 | 5 | 6 | 7 | 8 | 9 | 10 |
|---|---|---|---|---|---|---|---|---|---|---|
| Ammonium Xylene Sulfonate | QS | QS | QS | QS | QS | QS | QS | QS | QS | QS |
| Water | QS | QS | QS | QS | QS | QS | QS | QS | QS | QS |

(1) Cationic Galactomannan (with Mol. W. of ~200,000; Char. Den. = 3.0 meq/g)
(2) Cationic Galactomannan (with Mol. W. of ~200,000; Char. Den. = 0.7 meq/g)
(3) Jaguar C17 available from Rhodia
(4) ADPP-5043HMW (with Mol. W. of ~1,200,000 and Char. Den. of 2.0 meq/g) available from Aqualon/Hercules
(5) Polymer LR30M available from Amerchol/Dow Chemical
(6) Viscasil 330M available from General Electric Silicones
(7) DC-1664 Silicone Emulsion available from Dow Corning
(8) DC-1872 Silicone mirco-emulsion available from Dow Corning All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shampoo composition comprising:
   a) from about 5% to about 22% of one or more anionic detersive surfactants, by weight of said shampoo composition;
   b) from about 5 to about 40% by weight of said shampoo composition of a pre-formed solid crystalline gel network phase consisting of:
      i) from about 0.05% to about 14% of one or more fatty alcohols having about 16 to about 22 carbon atoms;
      ii) from about 0.3% to about 5% of one or more surfactants selected from the group consisting of cationic surfactants, anionic surfactants, non-ionic surfactants, zwiterionic surfactants, amphoteric surfactants, and mixtures thereof, by weight of said shampoo composition; and
      iii) water;
   c) from about 0.05% to about 5%, by weight of the shampoo composition, of a galactomannan polymer derivative with a net positive charge and having a mannose to galactose ratio of greater than 2:1 on a monomer to monomer basis, wherein the galactomannan polymer derivative has:
      i) a molecular weight from about 1,000 to about 10,000,000; and
      ii) a cationic charge density from about 0.7 meq/g to about 7 meq/g;
   d) from about 0.01% to about 10% by weight of the composition of a silicone conditioning agent; and
   e) from about 20% to about 95% of an aqueous carrier, by weight of said shampoo composition.

2. A shampoo composition according to claim 1, wherein said surfactant is selected from the group consisting of cationic surfactants, anionic surfactants, and mixtures thereof.

3. A shampoo composition according to claim 2, wherein said cationic surfactant is selected from the group consisting of cetrimonium chloride, behentrimonium chloride, distearyldimonium chloride, and mixtures thereof.

4. A shampoo composition according to claim 2, wherein said anionic surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and mixtures thereof.

5. A shampoo composition according to claim 1, further comprising an additional component selected from the group consisting of deposition aids, dispersed particles, nonionic polymers, additional conditioning agents, anti-dandruff actives, humectants, suspending agents, perfumes, amino acids, and water-insoluble vitamins.

6. A shampoo composition according to claim 5, wherein said suspending agent is a crystalline suspending agent.

7. A shampoo composition according to claim 5, wherein said silicone conditioning agent has a particle size as measured in said shampoo composition from about 0.01 μm to about 50 μm.

8. A shampoo composition according to claim 7, wherein said silicone conditioning agent has a particle size as measured in said shampoo composition from about 0.01 μm to about 2 μm.

9. A method of treating hair, said method comprising the step of applying to the hair a shampoo composition according to claim 1.

* * * * *